United States Patent
Gu et al.

(10) Patent No.: US 7,502,106 B2
(45) Date of Patent: Mar. 10, 2009

(54) SERS ANALYZER

(75) Inventors: Yuandong Gu, Plymouth, MN (US);
James A. Cox, New Brighton, MN (US);
Barrett E. Cole, Bloomington, MN (US)

(73) Assignee: Honeywell International Inc.,
Morristown, NJ (US)

( * ) Notice: Subject to any disclaimer, the term of this patent is extended or adjusted under 35 U.S.C. 154(b) by 0 days.

(21) Appl. No.: 11/533,984

(22) Filed: Sep. 21, 2006

(65) Prior Publication Data

US 2008/0074662 A1    Mar. 27, 2008

(51) Int. Cl.
*G01J 3/44* (2006.01)
*G01N 21/65* (2006.01)

(52) U.S. Cl. ...................................................... 356/301
(58) Field of Classification Search .................. 356/301
See application file for complete search history.

(56) References Cited

U.S. PATENT DOCUMENTS

| | | | |
|---|---|---|---|
| 5,255,067 | A | 10/1993 | Carrabba et al. |
| 5,266,498 | A | 11/1993 | Tarcha et al. |
| 6,028,666 | A | 2/2000 | Boss et al. |
| 6,040,191 | A | 3/2000 | Grow |
| 6,043,034 | A | 3/2000 | Takama et al. |
| 6,149,868 | A | 11/2000 | Natan et al. |
| 6,174,677 | B1 | 1/2001 | Vo-Dinh |
| 6,219,137 | B1 | 4/2001 | Vo-Dinh |
| 6,406,777 | B1 | 6/2002 | Boss et al. |
| 6,514,767 | B1 | 2/2003 | Natan |
| 6,623,977 | B1 | 9/2003 | Farquharson et al. |
| 6,649,683 | B2 | 11/2003 | Bell |
| 6,699,724 | B1 | 3/2004 | West et al. |
| 6,858,372 | B2 | 2/2005 | Whitlock et al. |
| 6,878,184 | B1 | 4/2005 | Rockenberger et al. |
| 6,947,132 | B1 | 9/2005 | Boss et al. |
| 7,019,828 | B2 | 3/2006 | Su et al. |
| 2003/0186240 | A1* | 10/2003 | Su et al. ..................... 435/6 |
| 2003/0187237 | A1 | 10/2003 | Chan et al. |
| 2004/0023411 | A1 | 2/2004 | Fenn |
| 2004/0038255 | A1 | 2/2004 | Mirkin et al. |
| 2004/0086897 | A1 | 5/2004 | Mirkin et al. |

(Continued)

OTHER PUBLICATIONS

Bizzarri et al., "Surface-Enhanced Resonance Raman Spectroscopy Signals from Single Myoglobin Molecules," Applied Spectroscopy, vol. 56, pp. 1531-1537, 2002.

(Continued)

*Primary Examiner*—F. L. Evans
*Assistant Examiner*—Abdullahi Nur
(74) *Attorney, Agent, or Firm*—Kris T. Fredrick

(57) ABSTRACT

A surface enhanced Raman scatter (SERS) analyte analyzer. The analyzer has floating surfaces for enhancement of the Raman scattered light from sample molecules. An injector may provide a spray of charged nanoparticles suspended in droplets of an evaporable solution into a chamber. When the solution quickly evaporates, droplets of nanoparticles are left without a supporting solution. These droplets or cloud of charged nanoparticles may then explode into a dispersion or aerosol. The charged nanoparticles may attract molecules of a sample for attachment to their surfaces. A laser light may impinge the attached molecules which may result in surface enhanced Raman scattered light received by a detector or a light spectrometer. Wavelength signatures may then be obtained from the spectrometer. The signatures may provide information about the molecules.

20 Claims, 4 Drawing Sheets

U.S. PATENT DOCUMENTS

| | | |
|---|---|---|
| 2004/0109386 A1 | 6/2004 | Gold et al. |
| 2004/0110208 A1 | 6/2004 | Chan et al. |
| 2004/0174520 A1 | 9/2004 | Premasiri et al. |
| 2004/0191669 A1 | 9/2004 | Whitlock et al. |
| 2005/0147963 A1 | 7/2005 | Su et al. |
| 2005/0147980 A1 | 7/2005 | Berlin et al. |
| 2005/0191665 A1 | 9/2005 | Su et al. |
| 2005/0196870 A1 | 9/2005 | Sun |
| 2005/0201941 A1 | 9/2005 | Cho et al. |
| 2005/0226938 A1 | 10/2005 | Borbely et al. |
| 2006/0061762 A1 | 3/2006 | Dwight et al. |
| 2006/0093750 A1* | 5/2006 | Han et al. .................. 427/458 |

OTHER PUBLICATIONS

Cooks et al., "Ambient Mass Spectrometry," Science, vol. 311, pp. 1566-1570, Mar. 17, 2006.

Elechiguerra et al., Interaction of silver nanoparticles with HIV-1, Journal of Nanobiotechnology, pp. 1-10, Mar. 28, 2005.

Etchegoin et al., New limits in ultrasensitive trace detection by surface enhanced Raman scattering (SERS), Elsevier Science B.V., pp. 84-90, Jan. 6, 2003.

Kelly et al., "The Optical Properties of Metal Nanoparticles: The Influence of Size, Shape, and Dielectric Environment," J. Phys. Chem B, vol. 107, No. 3, pp. 668-677, Aug. 9, 2003.

Kneipp et al., "Surface-Enhanced Raman Spectroscopy in Single Living Cells Using Gold Nanoparticles," Applied Spectroscopy, vol. 56, No. 2, pp. 150-154, 2002.

Li et al., "Electroreduction Activity of Hydrogen Peroxide on Pt and Au Electrodes," American Chemical Society, vol. 21, No. 20, pp. 9251-9259, 2005.

Ooka et al., "Surface-Enhanced Raman Spectroscopy of DOPA-Containing Peptides Related to Adhesive Protein of Marine Mussel, *Mytilus edulis*," Biopolymers, vol. 57, pp. 92-102, 2000.

Sengupta et al., "Surface-Enhanced Raman Spectroscopy of Bacteria and Pollen," Applied Spectroscopy, vol. 59, No. 8, 2005.

Real-Time Analyzers, "Simple SERS Sample Vials," 2 pages, Mar. 3, 2003.

Wilke et al., "Surface-Enhanced Raman Spectroscopy as a Probe of Adsorption at Transition Metal-High-Pressure Gas Interfaces: NO, CO, and Oxygen on Platinum-, Rhodium, and Ruthenium-Coated Gold," American Chemical Society, vol. 7, No. 4, pp. 714-721, 1991.

Zeng et al., "Electro-Hydrodynamic Modeling of Electrospray Ionization: CAD for a Fluidic Device—Mass Spectrometer Interface," 5 pages, prior to Sep. 21, 2006.

Moskovits, "Surface-enhanced Raman spectroscopy: a brief retrospective," Journal of Raman Spectroscopy, 36, pp. 485-496, 2005.

Ruan et al., "Surface-enhanced Raman scattering for perchlorate detection using cystamine-modified gold nanoparticles," Analytica Chimica Acta, 567, pp. 114-120, 2006.

* cited by examiner

SERS ANALYZER

BACKGROUND

The invention relates to analyzers and particularly to light scattering analyzers. More particularly, the invention pertains to Raman light scattering analyzers.

SUMMARY

The invention is an analyzer based on electro-spray ionization and surface enhanced Raman scattering.

DESCRIPTION

The breath of a person may contain rich information about that person, which may include the person's well being, nutrition, dietary habits, and so forth. A monitoring of the content of breath may offer great potential in clinical diagnosis, monitory ring, forensic science, and other fields. However, current technology such as mass spectroscopy, FTIR, colorimetry, and other technologies have limitations such as labeling required, non-real time measurements, difficulties of miniaturization, and more.

One may propose to integrate an electrical spray ionization device (ESI) based real-time nanoparticle sprayer with a surface enhanced Raman scattering (SERS) light source and detector for breath analysis. A nanoparticle solution may be made up of multiple types of functionalized nanoparticles with suitable solvent. During a spray, nanoclusters may be formed and analytes from a breath may bond or attach to the nanoparticles of the nanoclusters. A SERS signal may then be detected. This technique may feature miniaturizable, label-free, real-time, high sensitivity, and multiplexing. An example application of the present approach may include a portable ESI-SERS based breath analyzer. This analyzer may be used in clinics, resource-limited areas for disease monitoring, exposure identification, and so on.

Figure 1:
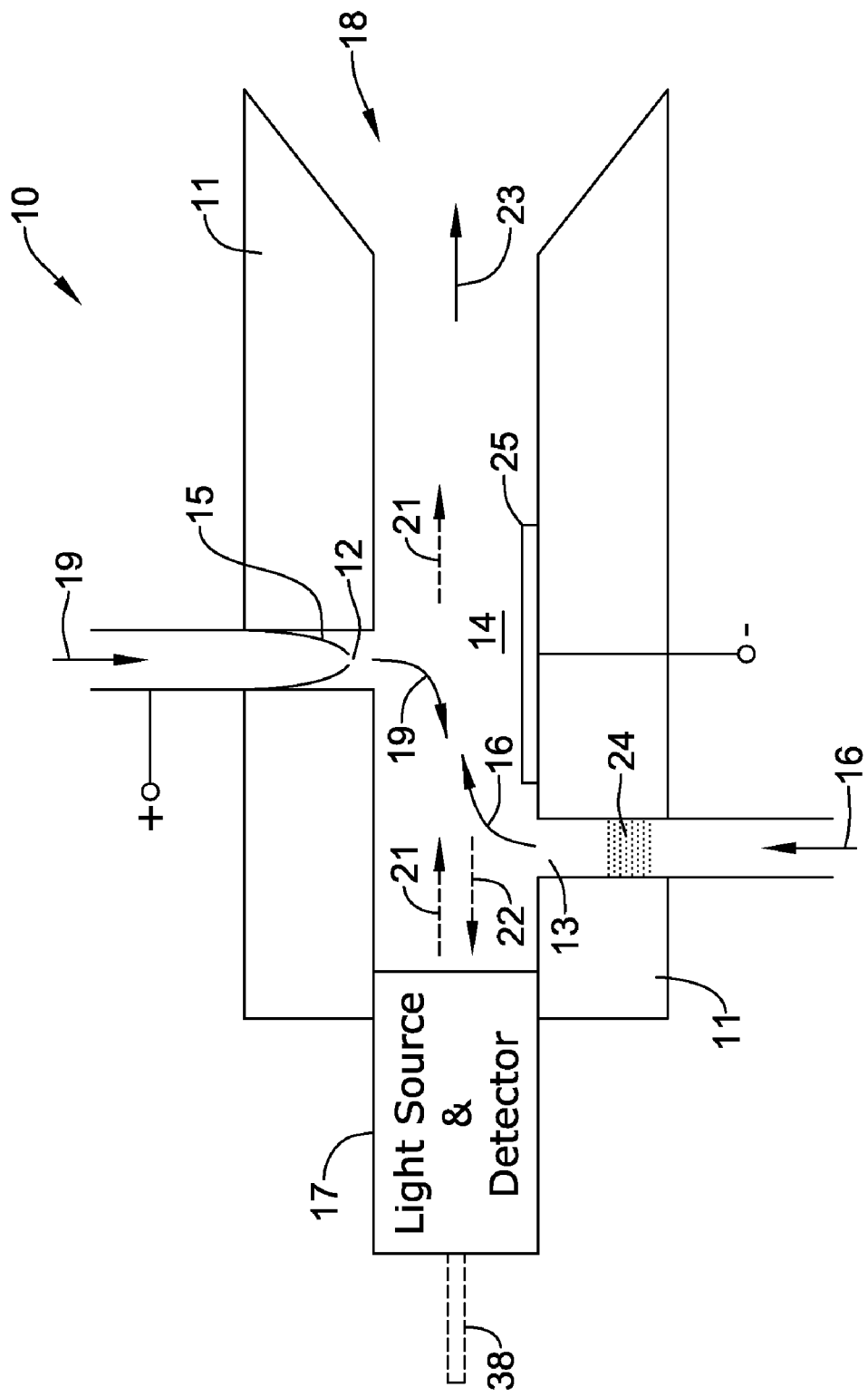
FIG. 1 is a diagram of a basic layout of the present analyzer.

FIG. 1 is a diagram of an illustrative implementation of the present invention. This implementation may be a breath analyzer 10. Analyzer 10 may have a support structure 11 which may contain a port 12 for an injection of a nanoparticle spray 19 from an ESI nozzle 15 through the port into a chamber 14. Another port 13 may be an inlet for conveying a sample of analyte 16, such as a breath or some other matter for analysis into the chamber 14. The analyte 16 and the spray 19 may combine into a combination 23 of analyte 16 with molecules attached to the nanoparticles 28 from the spray 19. Port 13 may have an applicable mechanism 24 for conditioning the matter containing analyte 16, such as a breath. Mechanism 24 may be, for example, a filter for removing particles and moisture from the sample. There may be a light source and detector 17 situated at one end of chamber 14 for emanating a light 21 and detecting light 22 scattered by the combination 23. The emanated light 21 and detected light 22 may be provided to and conveyed from the chamber 14, respectively, with an optical fiber or other mechanism 38. At the other end of chamber 14 may an outlet 18 for an exhaust of the product 23 of matter 16 and nanoparticles 28. A voltage may be applied across a metal pad 25 and nozzle 15, with the positive polarity connected to the nozzle. The polarity could instead be applied in reverse.

Figure 2:
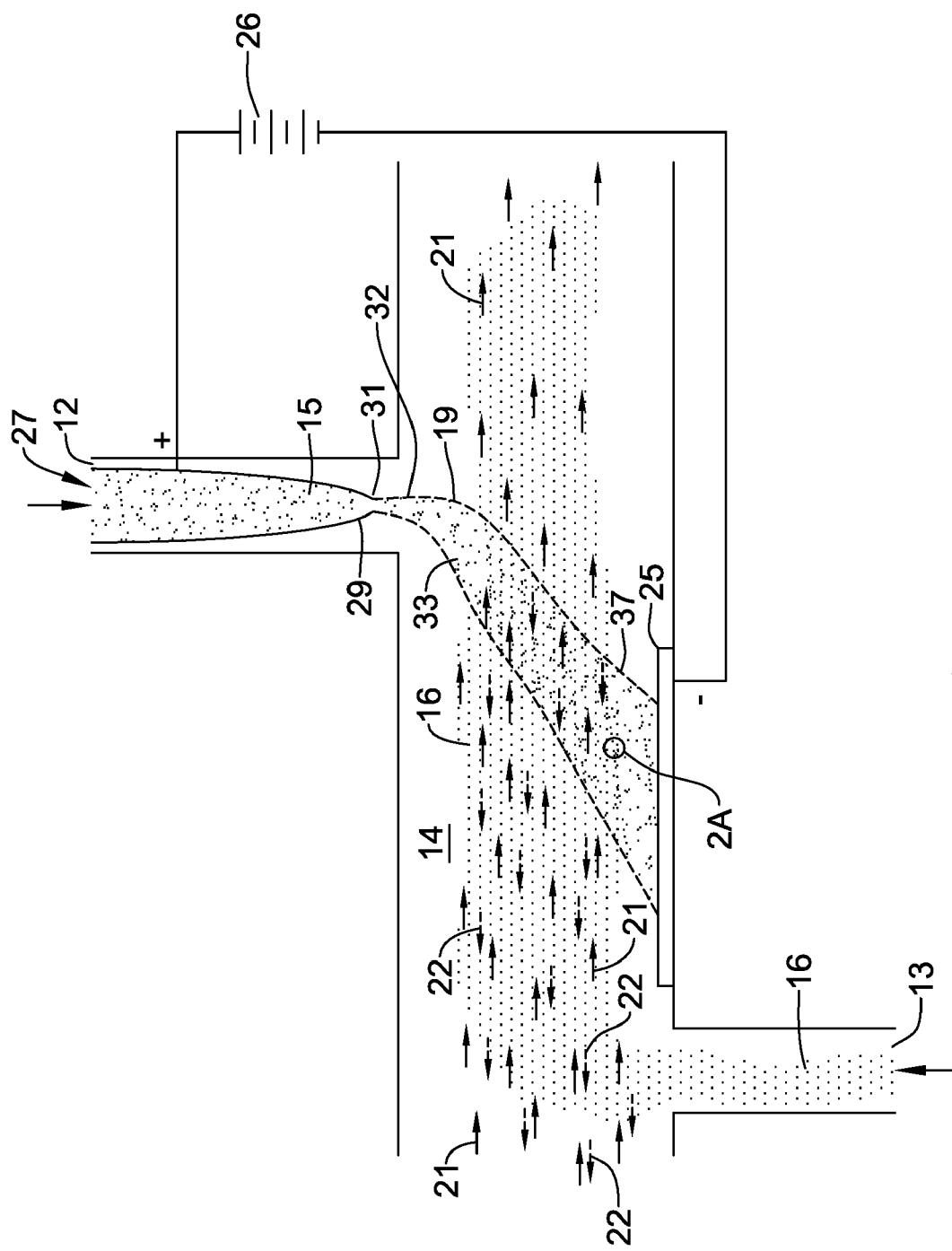
FIG. 2 is a diagram showing a chamber having inputs for a sample and nanoparticle solution, and an evolving nanoparticle droplet.
Figure 2A:
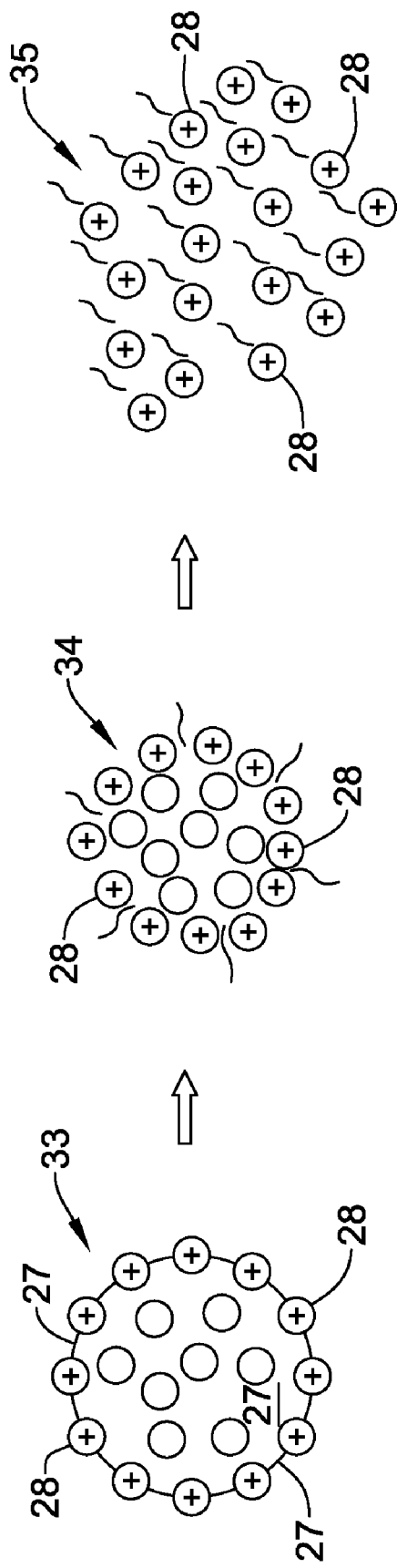

FIG. 2 reveals further details of the present system 10. A D.C. voltage source 26 of about 1000 volts may have a positive terminal connected to the nozzle 15 and a negative terminal connected to the cathode pad 25. Source 26 may be a battery or some other provision. A colloid of silver (Ag) nanoparticles 28 suspended in a solution 27 may be provided to nozzle 15 in the port 12. Other metals, in addition to silver, such as gold, copper, and/or other noble metals, may be used as nanoparticles. This colloid of nanoparticles may be pushed through the nozzle 15 which may have a needle-like exit tip 29. The solution 27 may have nanoparticles 28 with positive charges (i.e., like ions) due to the positive voltage applied to the metal nozzle 15 relative to the cathode pad or plate 25 which may be connected to an electric charge generator or source. The solution or fluid may flow out of the tip in a form of a capillary jet 32 with a cone-shaped base 31 at the tip of the nozzle that narrows down to a fine liquid filament or jet 32. The base 31 form of the exiting solution may be regarded as a Taylor cone. There may be a spraying of SERS-active nanoparticles 28 suspended in the solution 27. Interfacial instabilities may break this filament 32 into droplets 33 of charged Ag nanoparticles 28 to form a plume 37. The solution may rapidly evaporate resulting in droplets without solution or cloud 34 of nanoparticles 28 in the plume 37. Each droplet 34 may subsequently result in a (Coulombic) break up or explode into individually bare and charged Ag nanoparticles 28 as shown in a dispersion 35 of particles 28 in FIG. 3. The nanoparticles of this nature may be regarded as being aerosolized or an aerosol 35.

Figure 3:
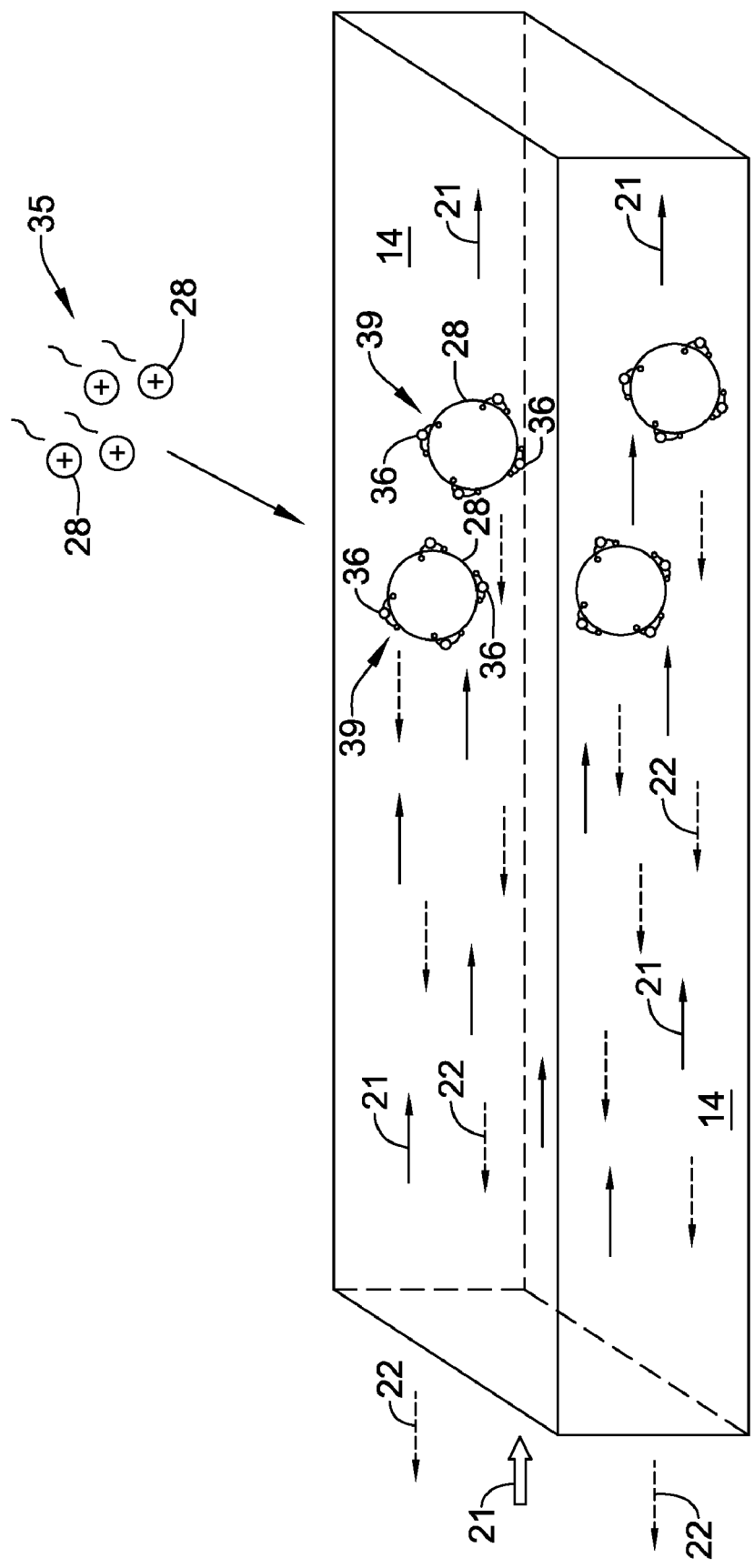
FIG. 3 reveals the chamber with an interaction of the analyte with nanoparticles.

An illustrative purpose of these nanoparticles 28 of chamber 14 is shown in FIG. 3. Molecules 36 from the sample 16, such as a breath, may attach to the charged Ag nanoparticles 28 floating in a vacuum, air or the like, in chamber 14. The nanoparticles 28 may be effectively an aerosol that constitutes a floating substrate for surface enhanced Raman scattering (SERS). There may be a flow of nanoparticles 28, many with molecules 36 attached, (e.g., nanoparticle attached molecule ensembles 39), towards the exhaust port 18 of FIG. 1.

Light 21, such as laser light, may be directed at one or more molecules 36 attached to the surfaces of nanoparticles 28. Enhanced surface Raman scattered light 22 may exit from the molecules 36 chamber 14 to a light spectrometer, e.g., a Raman spectrophotometer. SERS signatures may be read from the spectrometer, which may provide information about and/or identify the respective molecules 36.

To lead into a background of the present system, it may be noted that when light is scattered from an atom or molecule, most photons are elastically scattered (i.e., Rayleigh scattering). The scattered photons may have the same frequency as the incident photons. However, a small fraction of light (e.g., about 1 in $10^7$ photons) may be scattered at frequencies different from the frequency of the incident photons. This may be a result of inelastic scattering. Such scattered light may provide information about the molecules vibrational quantum states. Although Raman scattering may occur with a charge in vibrational, rotational or electronic energy of a molecule; a primary concern is the vibrational Raman effect.

There may be several kinds of Raman scattering. If a molecule absorbs energy (i.e., the resulting photon has lower energy), then one has Stokes scattering. If the molecule loses energy (i.e., the resulting photon has higher energy), then one has anti-Stokes scattering. The Stokes spectrum may be more intense than the anti-Stokes spectrum since a Boltzmann distribution may indicate that more molecules occupy lower energy levels than the higher levels in most cases. An absolute value should not depend on Stokes or anti-Stokes scattering. The energies of the different vibrational levels are of significance. The intensities of the Raman bonds may be dependent just on a number of molecules occupying different vibrational states, when the scattering process occurs.

The rather weak Raman effect or scattering (i.e., relative to the Rayleigh scattering) from molecules may be greatly strengthened (by a factor of up to 14 orders of magnitude) if the molecules are attached to a surface such as that of metallic nanostructures, e.g., colloidal silver particles. This phenomenon of increased intensity of Raman scattering may be referred to as surface-enhanced Raman scattering (SERS) which appears strongest on silver, but is observable on gold and copper.

Surface-enhanced Raman scattering may arise from several mechanisms. One may be an enhanced electromagnetic field produced at the surface of the metal. When the wavelength of the incident light is close to the plasma wavelength of the metal, conduction electrons in the metal surface may be excited into an extended surface electronic excited state called a surface plasmon resonance. Molecules adsorbed or in close proximity to the surface may experience an exceptionally large electromagnetic field. Vibrational modes normal to the surface tend to be most strongly enhanced.

Another mode of enhancement may be by a formation of a charge-transfer complex between the surface and the analyte molecule. Electronic transitions of many charge transfer complexes may be in the visible range, where a resonance enhancement can occur.

Molecules with a lone pair electrons or pi clouds may show the strongest SERS. The effect was apparently noted with pyridine. Aromatic nitrogen or oxygen containing compounds, such as aromatic amines or phenols, may be strongly SERS active. The effect may also be seen with other electron-rich functionalities such as carboxylic acids.

The intensity of a surface plasmon resonance may be dependent on many factors including the wavelength of incident light and the morphology of the metal surface. The wavelength should match the plasma wavelength of the metal. This wavelength may be about 382 nm for a 5 μm silver particle, but could be as high as 600 nm for larger ellipsoidal silver particles.

An advantage of the present invention may include a high capturing efficiency of high mono or poly molecules. Proteins, small molecules, pollen, anything that can flow through the chamber 14 in a gas phase, may be detected. An example application may include a sniffer. No sample preparation is necessarily needed. The particle capture may be 93 to 98 percent. The present system may be fluorescent signal insensitive. The high energy increase of the surface enhanced approach may be even greater with charged nanoparticles compared to the classical surface substrate approach of enhancement. That is because the molecules are drawn closer to a charged floating substrate, i.e., charged nanoparticles suspended in space. Detection of certain molecules may occur at as low as 30 ppt. The present system may operate at room temperature. It may used as a portable mass spectrometer. It can function with a flow rate of spray as low as one nL/min. Yet the air flow rate in the chamber may be as fast as meters per second. Consequently, an analysis may be fast (i.e., within milliseconds). For these and other reasons, the present system has advantages relative to the ordinary surface-enhanced Raman scattering approach.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A sample analyzer comprising:
   a chamber having a first end, a second end, a first input and a second input;
   a light source situated at the first end; and
   a detector situated at the first end; and
   wherein:
   the first input is for an injection of nanoparticles;
   the second input is for an insertion of a sample having molecules; and
   the nanoparticles are for attachment of the molecules, the nanoparticles becoming aerosolized nanoparticles and providing a floating surface for surface enhanced Raman scattering by molecules attached to the aerosolized nanoparticles.

2. The analyzer of claim 1, wherein:
   the light source is for impinging the molecules attached to the nanoparticles; and
   the detector is for receiving light scattered by the molecules.

3. The analyzer of claim 2, further comprising an electrical source for providing charges to nanoparticles.

4. The analyzer of claim 2, wherein the detector is for receiving Raman scattered light.

5. The analyzer of claim 2, wherein the detector is a light spectrometer.

6. The analyzer of claim 2, wherein the light source is a laser.

7. The analyzer of claim 4, wherein the effect of nanoparticles relative to the molecules is a surface enhanced Raman scattering.

8. The analyzer of claim 3, wherein the nanoparticles comprise silver, gold, copper, and/or other noble metals.

9. A method for analyzing a sample, comprising:
   providing a spray of charged surface enhanced Raman scattering (SERS) nanoparticles, wherein the nanoparticles of the spray are initially suspended in a solution; and
   the spray turns into droplets of nanoparticles in the solution;
   providing a sample having some molecules which attach to a charged SERS nanoparticle dispersion containing some of the nanoparticles, resulting in SERS nanoparticle attached molecule ensembles; and
   detecting surface enhanced Raman scattering from molecules of the SERS nanoparticle attached molecule ensembles.

10. The method of claim 9, wherein:
    the solution evaporates from the sprayed droplets containing SERS nanoparticles; and
    the sprayed droplets containing SERS nanoparticles eventually breakdown into a charged SERS nanoparticle dispersion.

11. The method of claim 9, further comprising, prior to the detecting, an impinging of the SERS nanoparticle attached molecule ensembles with a light beam.

12. The method of claim 9, wherein the detecting of the Raman scattering is effected with a spectrometer.

13. The method of claim 12, further comprising reading wavelength signatures from the spectrometer to identify one or more properties of some of the molecules attached to the nanoparticles.

14. A method for analyzing a sample, comprising:
   providing a spray of charged surface enhanced Raman scattering (SERS) nanoparticles;
   providing a sample, the sample comprising a breath, having some molecules which attach to a charged SERS nanoparticle dispersion containing some of the nanoparticles, resulting in SERS nanoparticle attached molecule ensembles; and
   detecting surface enhanced Raman scattering from molecules of the SERS nanoparticle attached molecule ensembles.

15. The method of claim 9, wherein nanoparticles comprise silver, gold, copper, and/or other noble metals.

16. A sample analyzer system comprising:
   a chamber;
   an injector having an end situated in the chamber;
   a sample port coupled to the chamber;
   a light source situated proximate to the chamber;
   a light detector situated proximate to the chamber; and
   a mechanism, connected to the injector, for providing nanoparticles suspended in an evaporable solution through the injector into the chamber, the nanoparticles becoming aerosolized nanoparticles and providing a floating surface for surface enhanced Raman scattering by molecules attached to the aerosolized nanoparticles.

17. The system of claim 16, further comprising:
   an electric charge source proximate to the chamber; and
   wherein:
   the electric charge source is for providing charges on the nanoparticles.

18. The system of claim 17, wherein:
   the light source is for emanating light which is scattered by some of the molecules attached to the nanoparticles; and
   the detector is for detecting surface enhanced Raman scattered light from some of the molecules attached to the nanoparticles.

19. The system of claim 18, wherein the detector is a spectrometer for detecting light wavelength signatures.

20. The system of claim 19, wherein the wavelength signatures are a basis for analysis and/or identification of the molecules.

* * * * *